United States Patent [19]

Sandel

[11] 4,418,821
[45] Dec. 6, 1983

[54] DISPOSABLE SURGICAL INSTRUMENT PLATFORM AND CONTAINER

[76] Inventor: Dan S. Sandel, 19524 Halsted St., Northridge, Calif. 91324

[21] Appl. No.: 336,034

[22] Filed: Dec. 31, 1981

[51] Int. Cl.³ .............................................. B65D 83/10
[52] U.S. Cl. .................................... 206/370; 206/570; 206/63.3; 206/460
[58] Field of Search .............. 206/570, 230, 370, 63.3, 206/460

[56] References Cited

U.S. PATENT DOCUMENTS

| | | | |
|---|---|---|---|
| 3,180,485 | 4/1965 | Nevitt | 206/370 |
| 3,780,857 | 12/1973 | Rosano, Jr. et al. | 206/370 |
| 3,944,069 | 3/1976 | Eldridge, Jr. | 206/63.3 |
| 4,013,109 | 3/1977 | Sandel | 206/370 |
| 4,151,913 | 5/1979 | Freitag | 206/370 |
| 4,182,448 | 1/1980 | Huck et al. | 206/63.3 |
| 4,254,862 | 3/1981 | Barratt | 206/63.3 |
| 4,318,473 | 3/1981 | Sandel | 206/370 |
| 4,344,532 | 8/1982 | Eldridge, Jr. et al. | 206/370 |

FOREIGN PATENT DOCUMENTS 200739 11/1958 Austria ............................. 206/370

Primary Examiner—Joseph Man-Fu Moy
Attorney, Agent, or Firm—Poms, Smith, Lande & Rose

[57] ABSTRACT

A disposable surgical instrument container has a foam block platform suitable for receiving portions of surgical instruments embedded therein and numeral indicia thereon to facilitate counting of such instruments, a magnetic strip to facilitate locating magnetic instruments thereon and a one piece sheet member having a plurality of panels divided by crease lines to facilitate folding of the panels into a folded vertically stacked configuration beneath the foam block platform to serve as a base for the platform and alternatively to be folded up about the platform in a container configuration for disposal of the platform and surgical instruments thereon. The foam block platform is of sufficient thickness to receive surgical instruments embedded therein and the panels are of sufficient width to extend upwardly over the platform when in folded up configuration to provide a surgical instrument containing chamber over an upper surface of the platform.

16 Claims, 5 Drawing Figures

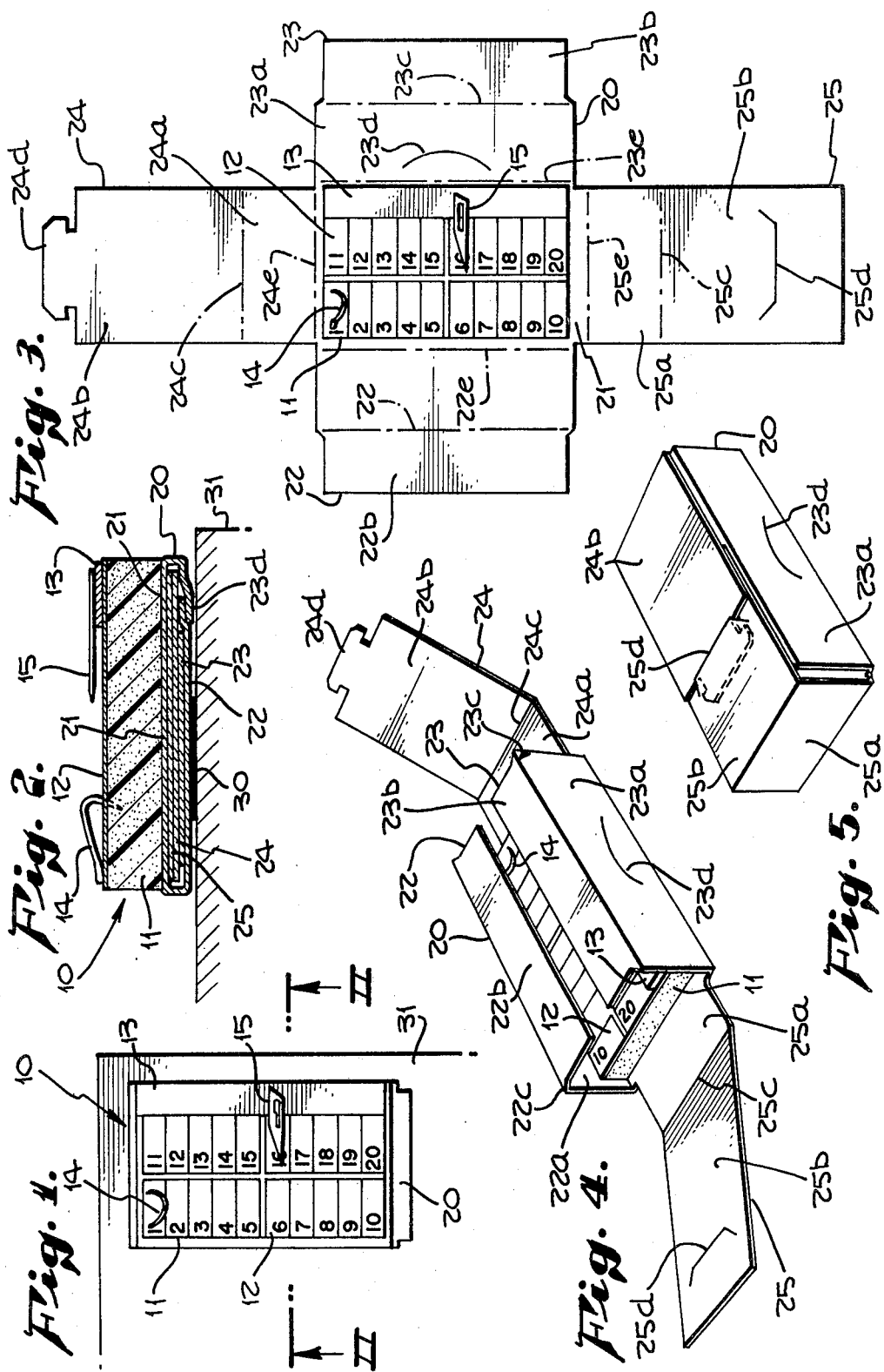

DISPOSABLE SURGICAL INSTRUMENT PLATFORM AND CONTAINER

BACKGROUND OF THE INVENTION

The present invention relates in general to disposable containers employed for counting and disposing of surgical instruments employed in surgery rooms in hospitals. More specifically, the present invention relates to a surgical instrument receiving and counting platform provided in association with a disposable enveloping container used for disposing of the surgical instruments after use in surgery operations.

It is common practice in modern hospital surgery room operation procedures to count the surgical instruments, such as surgical needles and blades, following use in surgery in order to account for all surgical instruments employed in the operation and thereafter to dispose of such instruments by placing them in containers which can be simply disposed of without reuse. Various types of disposable counting containers have been developed heretofore such as in my prior patent No. 4,013,109 and in my prior copending patent application Ser. No. 216,426 entitled Surgical Blade Removal and Disposal Device. In these prior disposable containers, the surgical instruments are retained within a plastic case having a relatively thin foam pad with or without a magnetic strip for locating counting and disposing of surgical instruments. I have found that it would be desirable to provide a more inexpensive, simpler disposable counting and disposing container to reduce the expense attendant a one time use and disposal device.

SUMMARY OF THE INVENTION

It is a primary object of the present invention to disclose and provide a disposable surgical instrument counting and container device which is initially free of covers, hinged container parts or other manipulative parts prior to use in counting surgical instruments and yet is provided with a container means suitable for enveloping the counting device and surgical instruments for disposal when desired. It is a further object to provide such a surgical instrument counting and disposable container device which is simple to manufacture and use, is less expensive than the container of my prior patent and application and which will facilitate the location, counting and subsequent disposal of surgical instruments in the environment of stressful conditions that can occur during handling of such instruments by personnel in hospital operating rooms during and immediately following surgery.

Generally stated, the present invention in disposable surgical instrument container device comprises the provision of a container means including a plurality of relatively foldable panels for being selectively and manually disposed in folded down stacked configuration and selectively in a folded up container like configuration, platform means preferably including a foam block of sufficient thickness for receiving surgical instruments in partially embedded relation thereon and means for securing the platform forming block to the container means so that the container means, when in folded down stacked for flat condition serves a base for the platform and when folded up in container like configuration serves as an already joined container enveloping the platform and surgical instruments thereon for disposal.

More specifically, the container means includes the provision of a one piece sheet of foldable panels including a center panel underlying and secured to an underside of the platform, a pair of side panels foldable up about sides of the platform and a pair of end panels foldable up about ends of the platform with the panels providing panel sections extending upwardly above the platform with folded over panel sections spaced above and overlying the upper surface of the platform to form an instrument containing chamber with the platform to facilitiate containing surgical instruments which may extend upwardly from the upper surface of the platform, as when a surgical needle has a sharp end embedded in the platform with other portions extending upwardly of the upper surface of the platform. Mechanical interlock means also are provided for facilitating holding the panels when in the folded down flat or stacked condition and for holding the panels in folded up condition. Adhesive means are provided for holding the platform and panels in the folded down or stacked configuration to a supportive surface in a fixed location.

It is submitted that those skilled in the art will obtain a better understanding of the present invention in disposable surgical instrument platform and container and will gain an appreciation of additional advantages and objects therefore from a consideration of the following detailed description of a preferred exemplary embodiment thereof. Reference will be made to the appended sheet of drawings which will first be briefly described.

BRIEF DESCRIPTION OF THE DRAWINGS

FIG. 1 is a plan view a preferred exemplary embodiment of disposable surgical instrument platform and container in accordance with the present invention shown with the container means folded flat beneath the platform means upon which surgical instruments are located;

FIG. 2 is a section view through the surgical instrument platform and container of claim 1 taken therein along the plane II—II FIG. 3 is a plan view of the surgical instrument form and container of claims 1 and 2 shown with the container means panels folded laterally outwardly from the folded flat position of FIGS. 1 and 2;

FIG. 4 is a perspective view of the surgical instrument platform and container of FIGS. 1 through 3 showing the container means in partially folded up configuration relative to the platform means; and FIG. 5 is a perspective view of the surgical instrument platform and container of FIGS. 1 through 4 shown with the container means in folded up container like configuration about the enveloped platform means and surgical instruments located thereon ready for disposal.

DETAILED DESCRIPTION OF A PREFERRED EXEMPLARY EMBODIMENT

Referring initially to FIG. 1, an exemplary embodiment of disposable surgical instrument platform and container, in accordance with the present invention, is illustrated generally at 10 and, in general, includes a platform 11 adhesively or otherwise secured to a folded container base 20. Platform 11 in the exemplary embodiment comprises a polystyrene foam block of sufficient thickness to receive surgical instruments partially embedded therein and having numerical indicia 12 printed directly thereon or printed on a thin film applied thereto. Preferably a magnetic strip 13 is provided along one side thereof. Surgical instruments such as the surgical needle 14 may be embedded in the foam block and a surgical blade 15 is shown magnetically held in stationary position by magnetic strip 13. Indicia 12 facilitate counting of the instruments on the upper surface of the platform 11.

A base supporting the platform 11 in a position of use, in the exemplary embodiment, comprises the folded container member or base 20 which is preferably provided in the form of a one piece cardboard like member having a plurality of panels susceptible of being folded in stacked relation beneath the platform 11 as seen in FIG. 2 or folded up in container like configuration thereabout as seen in FIG. 5.

Container base 20 in the exemplary embodiment includes a center panel 21 which is flat, underlies and is secured, as by suitable adhesive means, to the bottom surface of the platform 11. A left side panel 22 has an inner or lower panel section 22a an outer or upper panel section 22b and a fold or crease line 22c extending therebetween in the integral base 20. Similarly, a right side panel 23 is provided with a lower or inner panel section 23a, an upper or outer panel section 23b, a crease or dividing line 23c and a tab receiving slit 23d provided as part of a mechnical interlock means discussed hereinafter. Top end panel 24 is provided integrally of base 20 and includes an inner panel section 24a an outer panel section 24b, a dividing crease line 24c and a tab 24d. Bottom end panel 25, as seen in FIG. 3, includes an inner panel section 25a, an outer panel section 25b, a divider crease line 25c and a tab receiving slit 25d. As will be discussed hereinafter, and as seen in FIG. 5, tab 24d fits in slit 25d when the panels are in folded up container like configuration to hold the panels in such container like configuration. Adhesive means 30 are provided on the underside of the folded flat container base 20, as seen in FIG. 2, to hold the platform and container in a position of use on a supportive surface of a support such as table 31. Adhesive means may be a pressure sensitive contact adhesive normally covered by a thin sheet of plastic film, the latter being simply removed and the container merely pressed on a support surface.

The container means 20, in accordance with present invention, is normally folded flat beneath the platform 11 as seen in FIG. 2. Referring to the container means 20 in the fully opened position of FIG. 3, it is noted that the side panels 22 and 23 may be initially folded in overlapping relation beneath the center panel 21 with the end panels then being folded thereunder, end panel 25 being folded under first with end panel 24 being folded under subsequently to facilitate the making of a mechanical interlock through the interlock means of tab 24d and slit 25d. When initially folded into this stacked panel base configuration, the individual panels are generally in flat configurations with their panel sections remaining flat without there having been a bending or folding of the panel sections relative to one another along the crease lines 22c, 23c, 24c, 25c, although the panels having been bent relative to center section 21 along their respective inner edge crease lines 22e, 23e, 24e and 25e as seen in FIG. 3. Surgical needles and other sharp surgical instruments can be embedded in the foam block of platform 11 as seen in FIGS. 1 and 2 while surgical blades 15 can be located and counted by virtue of the indicia means 12 and the magnetic strip means 13. When it is desired to dispose of the platform and container, the panels 22, 23, 24 and 25 can be manually folded up about the platform 11 as now discussed.

Referring now to FIG. 4, it can be seen that in the exemplary embodiment the side panels 22 and 23 may be first folded up along their panel inner edge crease lines 22e and 23e to present the inner panel sections 22a and 23a in upwardly extending positions along sides of the foam block platform 11 and preferably extending upwardly above the upper surface of platform 11 to facilitate clearance over surgical instruments located thereon. The outer panel sections 22b and 23b may then be folded inwardly along their respective crease lines 22c and 23c as seen in FIG. 4. The end panels 24 and 25 may then be folded up over the platform and side panels as seen in a comparison of FIGS. 4 and 5. In FIG. 4, the end panels are being folded along their crease lines 24e and 25e relative to the center panel 21 and their outer panel sections 24b and 25b are being moved into overlying spaced relation relative an upper surface of the platform 11 and interlocked via the interlock means of tab 24d and slit 25d to provide the folded up container configuration of FIG. 5 with an instrument receiving chamber thus formed over the platform 11. The surgical instrument platform and container of the present invention in the folded up container like configuration of FIG. 5 can then be disposed of as is the practice following use of the surgical instruments in modern day hospital procedures.

Having thus described a preferred exemplary embodiment of disposable surgical instrument platform and container in accordance with the present invention, it should be understood by those skilled in the art that various modifications and alterations thereof may be made, that the various panel sections may be folded in other orders of panel folding sequences, that other materials can be used for the platform and container member, that various types of surgical instruments may be located thereon with portions embedded in the foam block where appropriate and that the present description is exemplary only of the present invention which is defined by the following claims.

I claim:

1. A disposable surgical instrument platform and container comprising:

an individual platform for receiving surgical instruments thereon and a folded container means for providing a supporting base for said platform while said platform receives surgical instruments thereon and for providing an enveloping container for said platform and surgical instruments for disposal thereof by being folded up about said platform, said container means comprising a one piece sheet of foldable panels including a center panel, a pair of side panels and a pair of end panels, all foldable into a first position of use wherein all of said panels are in a vertically aligned, stacked relation directly under and supporting said platform and being foldable into a second position of use wherein said center panel underlies said platform, said pair of side panels are foldable up about sides of said platform and said pair of end panels are foldable up about ends of said platform with said panels providing panel portions overlying and covering said platform upper surface.

2. The disposable surgical instrument platform and container of claim 1 wherein said platform means comprises:

numerical indicia means for locating and counting said instruments thereon.

3. The disposable surgical instrument platform and container of claim 1 wherein said platform means comprises:
magnetic means for holding a metallic surgical instrument placed thereon in a stationary position.

4. The disposable surgical instrument platform and container of claim 1 wherein said platform means comprises:
a foam block having sufficient thickness to receive the sharp ends of surgical instruments embedded therein with the remaining instrument portions extending vertically upwardly above said block.

5. The disposable surgical instrument platform and container of claim 1 wherein said container means comprises:
adhesive means for securing said folded flat container means on a support surface.

6. The disposable surgical instrument platform and container of claim 1 wherein said one piece sheet of foldable panels includes side and end panels having inner panel sections that fold up along crease lines at said center panel and extend upwardly along sides and ends, respectively, of said platform means to form an instrument receiving chamber above an upper surface thereof.

7. The disposable surgical instrument platform and container means of claim 6 wherein said one piece sheet of foldable panels further includes:
outer panel sections on said side and end panels that fold inwardly over said upper surface of said platform means at crease lines along upper edges of said inner panel sections of said side and end panels respectively.

8. The disposable surgical instrument platform and container of claim 7 wherein said one piece sheet of foldable panels further includes:
integral panel interlock means formed in two or more of said panels for holding said panels in folded up relation about said platform means.

9. The disposable surgical instrument platform and container of claim 1 wherein said container means comprises:
means for providing a surgical instrument containing chamber above said platform means.

10. The disposable surgical instrument platform and container of claim 10 wherein said chamber means comprises folded up and over panels of a one piece sheet member.

11. A disposable surgical instrument container comprising:
platform means for receiving surgical instruments in partially embedded relation thereon;
container means including a plurality of relatively foldable panels of a one piece sheet of foldable material divided by crease lines into a center, two side and two end panels for being selectively and manually disposed in folded down entirely lying under and in vertically stacked configuration and alternatively in a folded up container like configuration wherein said panels are folded up about sides and ends, respectively, of said platform means to form said container like configuration; and
means for securing said platform means to said container means when in folded down flat configuration whereby said container means can serve as a base for said platform means.

12. The disposable surgical instrument container of claim 11 wherein said platform means comprises:
foam block having sufficient thickness to receive the sharp ends of surgical instruments embedded therein.

13. The disposable surgical instrument container of claim 11 wherein adhesive means are provided for securing said container means to a supportive surface.

14. The disposable surgical instrument container of claim 13 wherein said adhesive means comprises the provision of a layer of pressure sensitive adhesive material in strip form on a portion of said container means.

15. The disposable surgical instrument container of claim 1 wherein said means for securing said platform means to said container means includes adhesive means securing a bottom surface of said platform means to said center panel of said one piece sheet.

16. The disposable surgical instrument container of claim 15 wherein said one piece sheet and its panels are so provided that a surgical instrument containing chamber is formed above an upper surface of said platform means within said folded up panels when in said container like configuration.

* * * * *